(12) United States Patent
Syed et al.

(10) Patent No.: US 7,875,427 B2
(45) Date of Patent: Jan. 25, 2011

(54) COMPOSITIONS AND METHODS FOR IL-13 BIOMARKERS

(75) Inventors: Farhat Syed, Audubon, PA (US); Chong C. Huang, Paoli, PA (US); Katherine Li, Wallingford, PA (US); Guihua Liu, Chadds Ford, PA (US); Xiaozhou Shang, West Chester, PA (US); Li Li, Downingtown, PA (US)

(73) Assignee: Centocor, Inc., Mavern, PA (US)

( * ) Notice: Subject to any disclaimer, the term of this patent is extended or adjusted under 35 U.S.C. 154(b) by 258 days.

(21) Appl. No.: 11/536,704

(22) Filed: Sep. 29, 2006

(65) Prior Publication Data

US 2007/0077585 A1 Apr. 5, 2007

Related U.S. Application Data

(60) Provisional application No. 60/722,296, filed on Sep. 30, 2005.

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS

| 5,853,697 | A | 12/1998 | Strober |
| 6,194,163 | B1 | 2/2001 | Doyle et al. |
| 2005/0036951 | A1 | 2/2005 | Henderson |

FOREIGN PATENT DOCUMENTS

| EP | 1347051 | 9/2003 |
| EP | 1394274 | 3/2004 |

OTHER PUBLICATIONS

Boutten et al., Thorax. Oct. 2004;59(10):850-4.*
Gebauer et al., Nat Rev Mol Cell Biol. Oct. 2004;5(10):827-35.*
Enric Espel, Semin Cell Dev Biol. Feb. 2005;16(1):59-67.*
Piecyk et al., EMBO J. Aug. 1, 2000;19(15):4154-63.*
Dejmek et al., Clin Cancer Res. Jan. 15, 2005;11(2 Pt 1):520-8.*
Fan et al., Eur Respir J. Nov. 2005;26(5):933-47.*
Kolls et al., Immunity. Oct. 2004;21(4):467-76.*
Oshima et al., FASEB J. Jun. 2001;15(8):1469-71.*
(1997) "National Institutes of Health. Guidelines for the Diagnosis and Management of Asthma. Rep. No. 97-4051. Washington DC: US.Dept.Health Human Serv., Nat'l. Heart & Lung Blood Inst."
(2001) "Biomarkers and Surrogate Endpoints: preferred definitions and conceptual framework". Clin. Pharmacol Ther 69(3): 89-95.
Akbari O,S.P., Meyer E., Kronenberg M, Sidobre S, Nakayama T, Taniguchi M, Grusby MJ, Dekruyff RH, Umetsu DT. (2003) "Essential role of NKT cells producing IL-4 and IL-13 in the development of allergen-induced airway hyperreactivity". Nat Med 9: 582-588.
Berkman, N.,S.Ohnona, et al. (2001). "Eotaxin-3 but Not Eotaxin Gene Expression is Upregulated in Asthmatics 24 Hours After Allergen Challenge". Am.J. Respir.Cell.Mol.Biol. 24(6): 682-687.
Elias J, Z.A. Chupp G., Homer R. (1999) "Airway Remodeling in Asthma". J Clin Invest 104(8): 1001-6.
Fahey, J. (2000) "Proceedings fo the ATS Workshop on Refactory Asthma: Current Understanding, Recommendations, and Unanswered Questions." Am. J. Respi. Crt. Care Md. 162(6):341-6.
Grunig G, W.M. Wakil AE, Venkayya R, Brombacher F, Rennick DM, Sheppard D, Mohrs M, Donaldson DD, Locksley RM, Corry DB. (1998). "Requirement for IL-13 Independently of IL-4 in Experimental Asthma". Science 282: 2261-2263.
Hijnen, D, M. De Bruin-Weller et al., (2004). "Serum Thymus and Activation-regulated Chemokine (TARC) and Cutaneous T Cell-Attracting Chemokine (CTACK) Levels in Allergic Diseases: TARC and CTACK are disease-specific markers for atopic dermatitis". Journal of Allergy and Clinical Immunology 113(2): 334-340.
Holgate, S. T. (1999) "The Epidemic of Allergy and Asthma", Nature 402: B2-B4.
Leung, T.F., C.K. Wong, et al. (2003). "Plasma TARC Concentration may be a Useful Marker for Asthmatic Exacerbation in Children". Eur Respir J 21(4): 616-620.
Pilette, C, J.N. Francis, et al. (2004). "CCR4 Ligands are Up-regulated in the Airways of Atopic Asthmatics after Segmental Allergen Challenge". Eur Respir J 23(6): 876-884.
Sekiya T., "Increased Levels of the TH2-Type CC Chemokine Thymus and Activaton-Regulated Chemokine (TAC) in Serum and Induced Sputum of Asthmatics", Allergy 2002 173-177.
Venkayya R, L.M., Willkom M, Grunig G, Corry DB, Erle DJ (2002). "The Th2 Lymphocyte Products IL-4 and IL-13 Rapidly Induce Airway Hyperresponsiveness through Direct Effects on Resident Airway Cells". Am J Respir Cell Mol Biol. 26: 202-208.
Walter DM, M.J., Berry G, Mc Kenzie AN, Donaldson DD, Dekruyff RH, Umetsu DT. (2001). "Critical Role for IL-13 in the Development of Allergen-Induced Airway Hyperreactivity". J Immunol 167: 4668-4675.
Wills-Karp M, L.J., Xu X, Schofield B, Neben TY, Karp CL, Donaldson, DD. (1998). "Interleukin-13: Central Mediator of Allergic Asthma". Science 282: 2258-2261.
Yang Gaoyun et al., "Anti-IL-13 monoclonal antibody inhibits airway hyperresponsiveness, inflammation and airway remodeling", Cytokine, vol. 28, No. 6 pp. 224-232, XP002542095 (2004).
Yuyama Noriko et al., Analysis of novel disease-related genes in bronchial asthma:, Cytokine, vol. 19, No. 6, pp. 287-296, XP002542097 (2002).
Lee et al., "Interleukin-13 induces dramatically different transcriptional programs in three human airway cell types", American Journal of Respiratory Cell and Molecular Biology, vol. 25, No. 4, pp. 474-485, XP002542098 (2001).
Syed et al, "Identification of interleukin-13 related biomarkers using peripheral blood mononuclear cells", Biomarkers, Taylor and Francis, London, GB, vol. 12, No. 4, pp. 4140423 XP008110155 (2007).

* cited by examiner

*Primary Examiner* — Zachary Skelding

(57) ABSTRACT

Compositions and methods are provided for measuring and determining biomarkers for IL-13.

6 Claims, 8 Drawing Sheets

Figure 1:
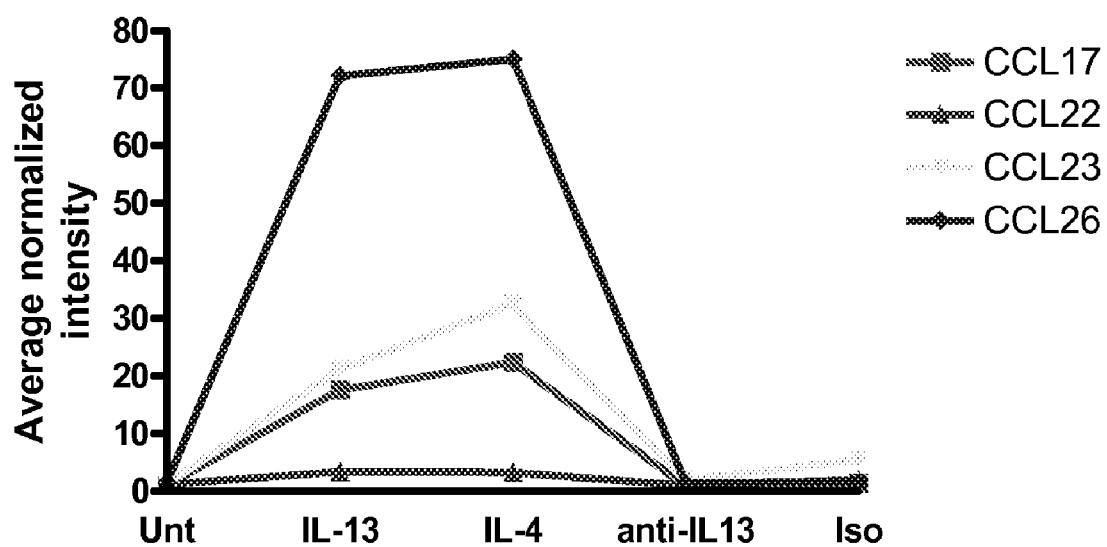
Figure 2A:
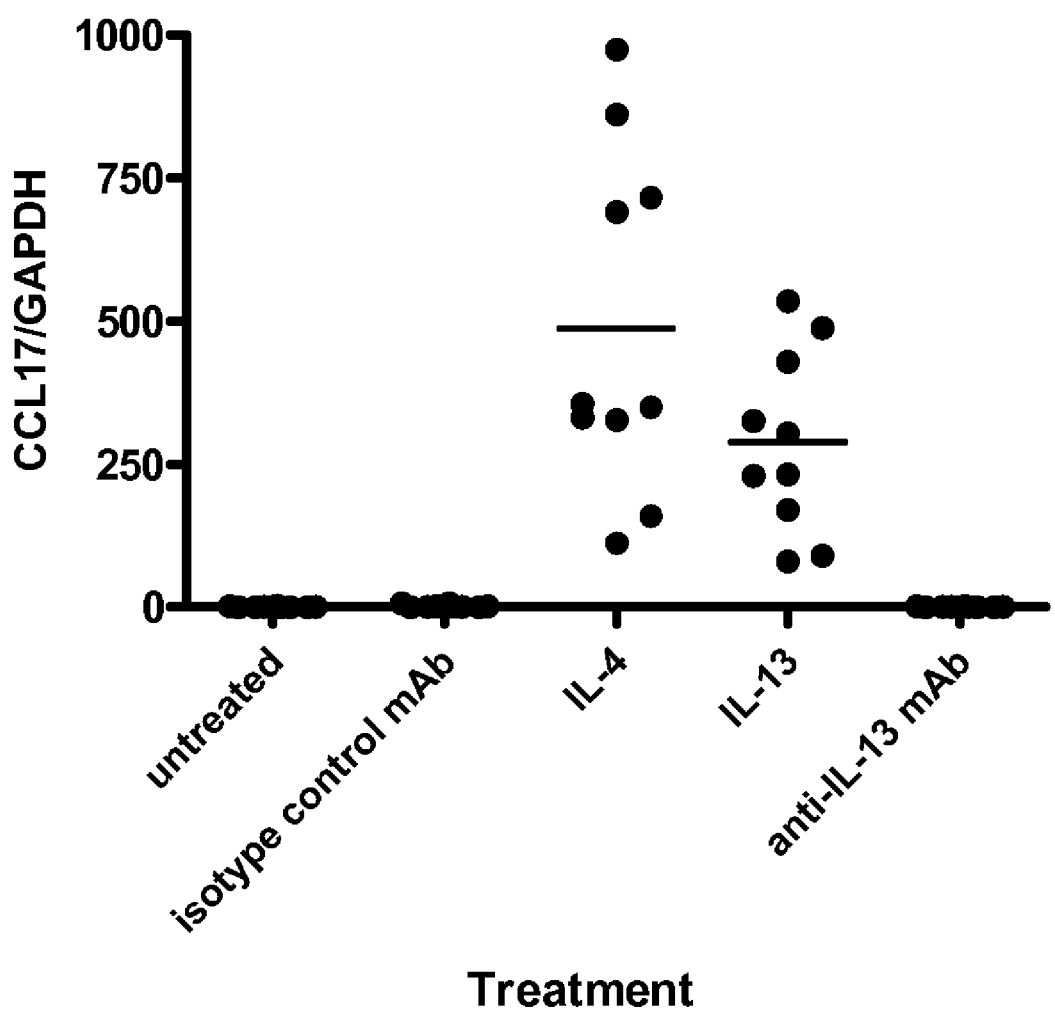
Figure 2B:
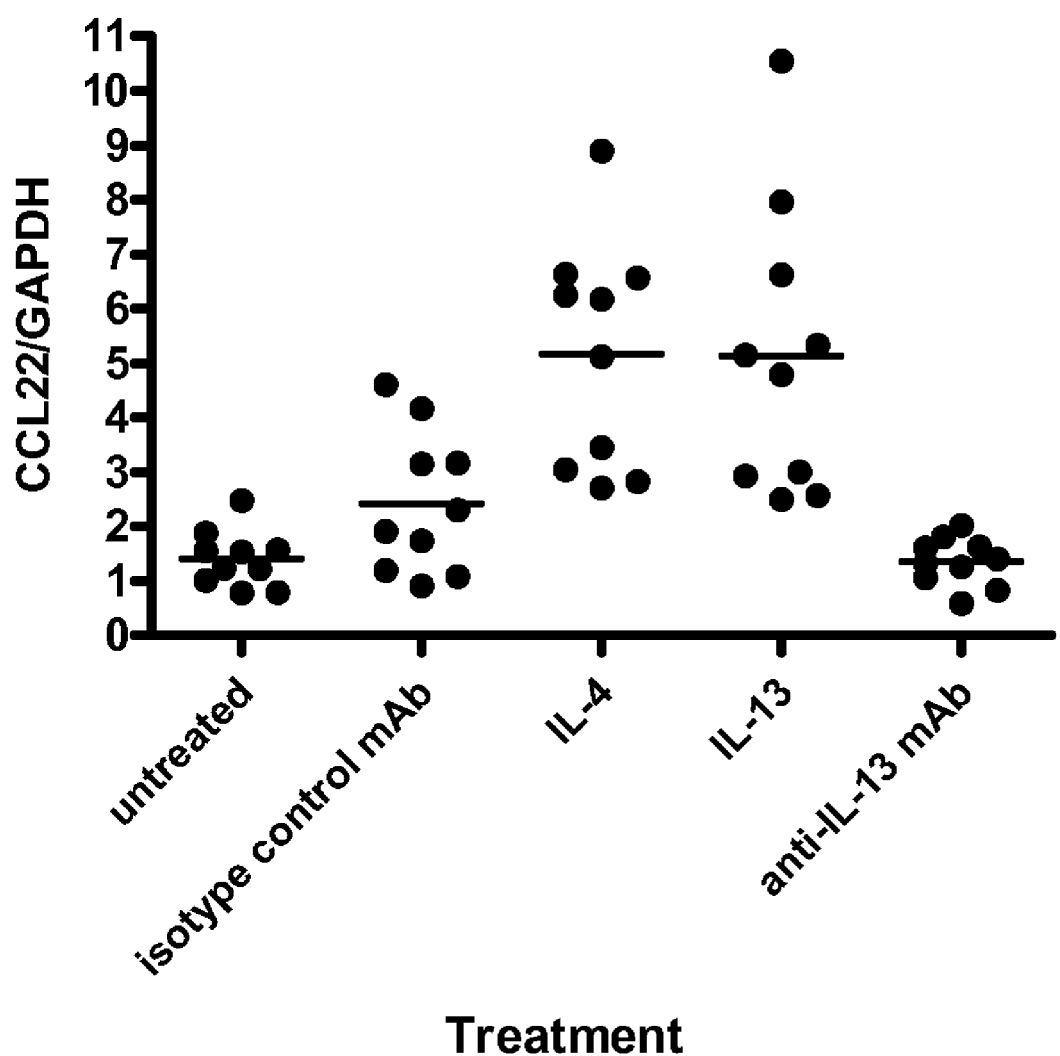
Figure 2C:
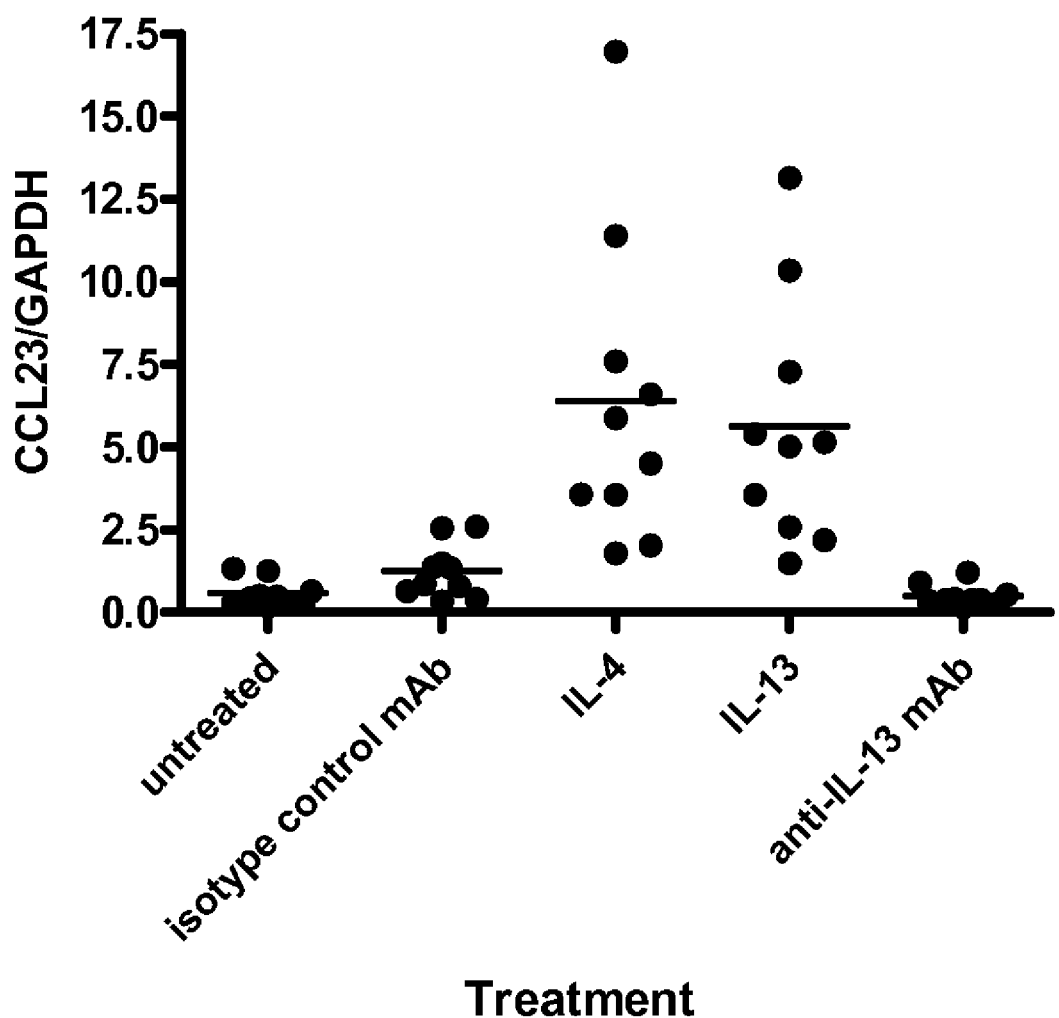
Figure 2D:
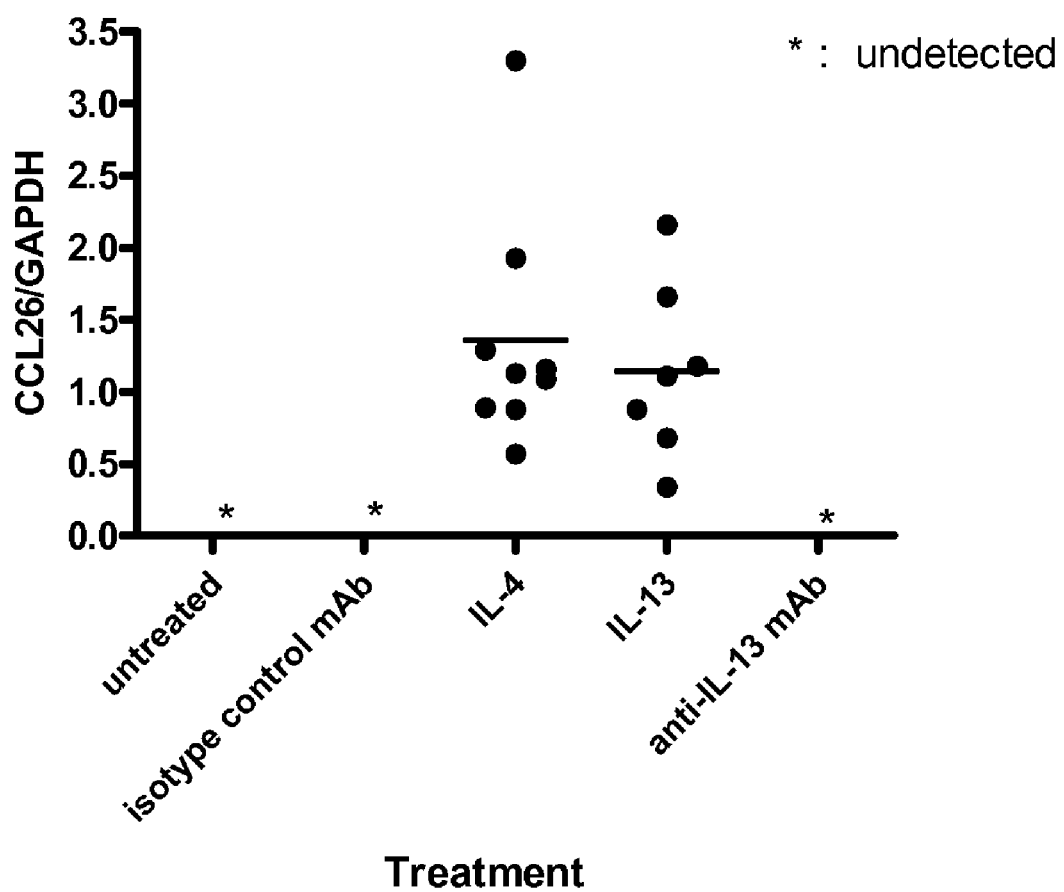

Figure 3(A) TARC concentration in PBMC culture supernatant (n=5 donors)
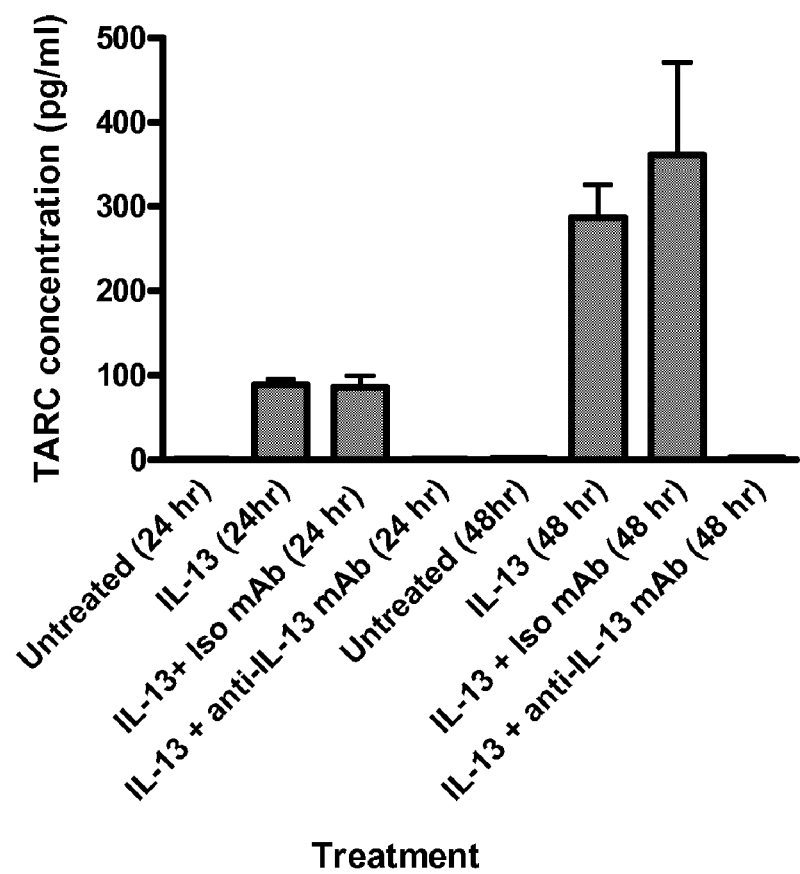

Figure 3(B) MDC concentration in PBMC culture supernatant (n=5 donors)
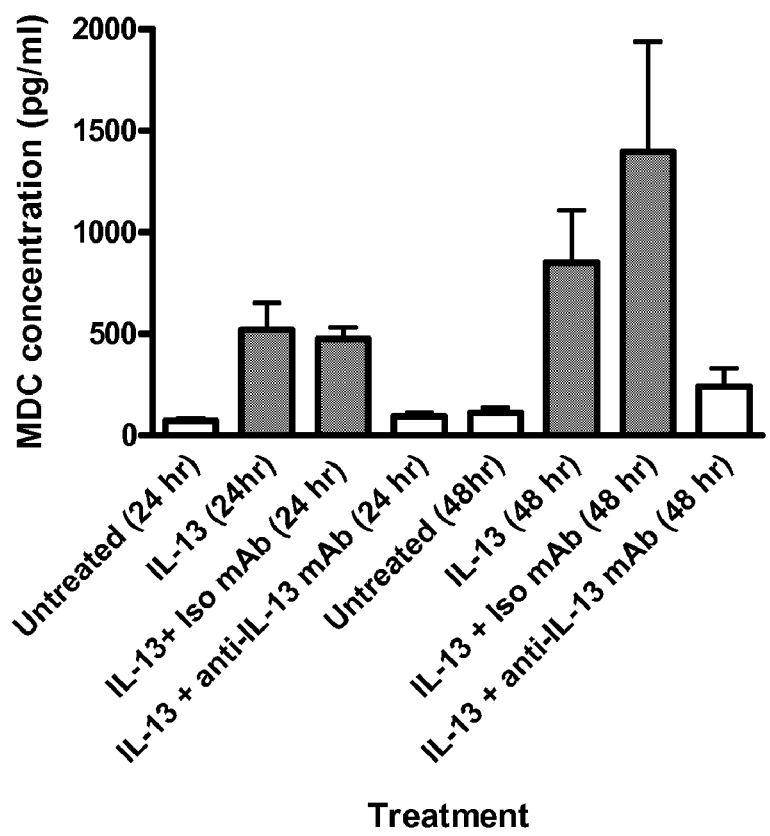

Figure 3(C) Eotaxin3 concentration in PBMC culture supernatant (n=5 donors)
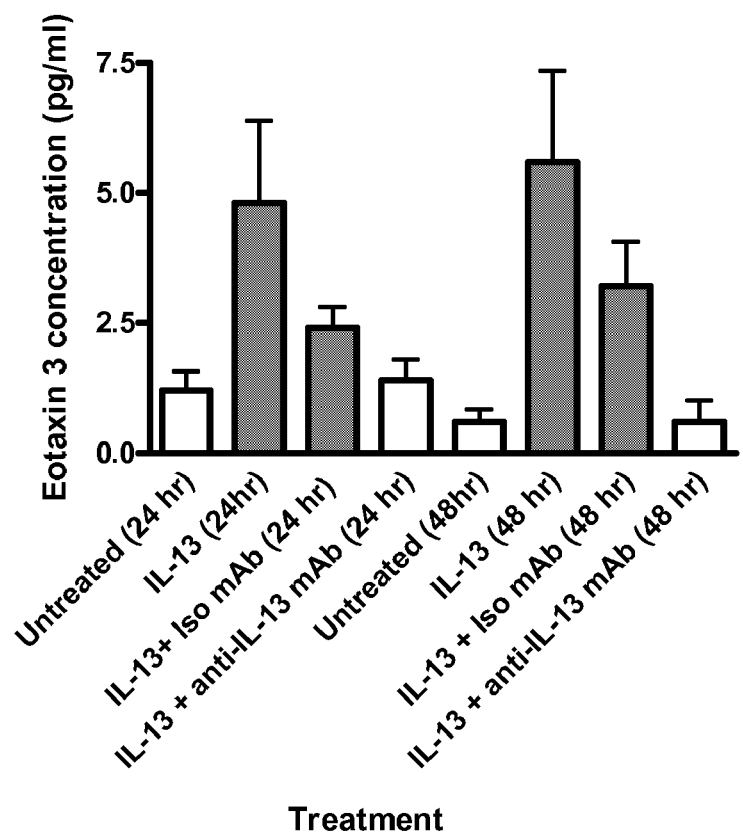

COMPOSITIONS AND METHODS FOR IL-13 BIOMARKERS

This application claims priority to U.S. application No. 60/722,296, filed Sep. 30, 2005, which is incorporated herein by reference.

BACKGROUND

The subject matter disclosed and claimed herein relates to methods for monitoring the biological response to IL-13 or IL-13 therapy using novel biomarkers for IL-13. This disclosure presents evidence that a panel of genes can be used as biomarkers in IL-13 studies for inflammatory disorders such as asthma, emphysema and chronic obstructive pulmonary disease (COPD), and may also play a role in other lung disorders with an inflammatory component. Of the panel of potential biomarkers described above, WNT5A and MPIF-1 (CCL23) have not been previously reported to be regulated by IL-13. These are novel IL-13 related biomarkers, which can be useful in any disease where IL-13 plays a major role.

Biomarkers can play a key role in identifying responders and non-responders to therapy and thereby lead to the development of more effective therapies. A number of studies have been described where microarray platform has been used to identify asthma and other inflammatory related signature genes.

The relevance of these genes to disease is very important for them to be effective biomarkers. To that end a number of the genes have been linked to diseases where IL-13 is believed to play a role. Increased level of TARC has been reported in serum and induced sputum of asthmatics (Sekiya, et al (2002), Allergy 57(2): 173-177.), plasma of children during asthma exacerbation (Leung et al., (2003), Eur. Respir J 21(4): 616-620.) and serum of patients with atopic dermatitis (Hijnen, et al., (2004), Journal of Allergy and Clinical Immunology 113(2): 334-340). This provides evidence that TARC might be involved in the pathogenesis of such disorders. Eotaxin 3 gene expression has been shown to be upregulated in bronchial biopsies of asthmatics after allergen challenge implying that Eotaxin 3 may be important in late-phase eosinophil recruitment to the airways of asthmatics (Berkman, et al. (2001), Am. J. Respir. Cell Mol. Biol. 24(6): 682-687). Also, CCL22 was shown to be up regulated in bronchoalveolar lavage (BAL) after a segmental allergen challenge of asthmatics (Pilette, et al. (2004), Eur Respir J 23(6): 876-884). Additionally, recent reports using murine models of allergic asthma have shown that the Th2 type cytokine IL-13 may play a critical role in the pathogenesis of asthma, either by regulating airway inflammation, mucus hyper-secretion or airway hyper-responsiveness thus making it an attractive target for therapeutic intervention.

The present invention provides a new approach to monitoring anti-IL13 therapy by detecting one or more biomarkers of IL-13, and IL-13 bioactivity. Described herein is a panel of potential biomarkers, associated with IL-13 biology, which can be useful in an anti-IL-13 clinical trial or for monitoring therapy using methods well known in the art. The panel of biomarkers can be used as a tool to monitor the efficacy of an anti-IL-13 therapeutic such as an IL-13 antagonist such as a small molecule or a biologic, and provide valuable information in terms of dosing amount and frequency.

SUMMARY OF THE INVENTION

Disclosed and claimed herein is the discovery of a panel of genes that can serve as biomarkers and may be useful in an anti-interleukin (IL)-13 trial.

The disclosed panel of genes responsive to IL-13 may be used in methods for diagnosing and tracking the efficacy of an anti-IL-13 therapy in IL-13 related disorders. These disorders include, but are not limited to, emphysema, asthma and chronic obstructive pulmonary disorder (COPD). Diagnostic and prognostic methods based on detecting and measuring expression of these IL-13 responsive genes, or protein, in a sample is also disclosed.

Specifically, described and claimed herein is a method of monitoring the response to anti-IL13 therapy in a patient undergoing such therapy by using one or more IL-13 biomarkers, which comprises: Determining the level of expression of at least one of WNT5A or MPIF-1 (CCL23) in a tissue sample of a patient; administering the anti-IL-13 therapy to the patient; measuring the level of at least one of WNT5A or MPIF-1 (CCL23) expression in said tissue of the patient and determining whether the anti-IL-13 therapy is effective in reducing the level of IL-13 or IL-13 related physiological effects.

The method can also include measuring at least one of the biomarkers CCL17 (TARC), CCL22 (MDC), CCL23 (MPIF-1) and CCL26 (Eotaxin 3), CD1A, CD1B, CD1C, IgE CD23A, IL-17Rbeta.

Several methods have been reported for the measurement of biomarker expression and any of these methods may be employed in the invention. These include (i) radioimmunoassays and single radial immunodiffusion procedures (Chambers, R. E. and Whicher, J. T. (1983); J. Immunol. Methods 59, 95; Marhaug, G. (1983) supra; Taktak, Y. S. and Lee, M. A. (1991); J. Immunol. Methods 136, 11); (ii) ELISA based assays (Zuckerman, S. H. and Suprenant, Y. M. (1986); J. Immunol. Methods 92, 3743; Dubois, D. Y. and Malmendier, C. L. (1988); J. Immunol. Methods 112, 71-75; Sipe, J. D. et al. (1989); J. Immunol. Methods 125, 125-135; Yamada, T. et al. (1989); Clin. Chim. Acta 179, 169-176; Tino-Casl, M. and Grubb, A. (1993); Arm. Clin. Biochem 30, 278-286); (iii) nephelometric methods (Vermeer, H. et al. (1990); Clin. Chem 36, 1192; Yamada, T. et al. (1993); Ann. Clin. Biochem. 30, 72-76); (iv) an electrophoretic procedure (Godenir, N. L. et al. (1985); J. Immunol. Methods 83, 217); (v) an immunochemiluminescence procedure (Hachem, H. et al. (1991); Clin. Biochem 24, 143-147); (vi) an automated method based on a monoclonal-polyclonal antibody solid phase enzymeimmunoassay (Wilkins, J. W. et al. (1994); Clin. Chem 40 (7), 1284-1290); and (vii) time-resolved fluorometric immunoassay (Malle, E., et al. (1995); J. Immunol. Methods 182, 131). See U.S. Pat. No. 6,194,163 which discloses a method for the quantitative measurement of human acute phase serum amyloid A protein.

DETAILED DESCRIPTION

Figure Descriptions

FIG. 1. Microarray data showing the average normalized intensity levels of CCL17, CCL22, CCL23 and CCL26 upon treatment of PBMCs from ten donors with IL-13, IL-4, anti-IL-13 mAb or isotype control mAb for 24 hrs.

FIG. 2. Real Time PCR (Taqman®) analysis showing the level of A) CCL17 B) CCL22C) CCL23 D) CCL26 upon treatment of PBMCs from ten donors with IL-13, IL-4, anti-IL-13 mAb or isotype control mAb for 24 hrs. The quantity of each gene is normalized to GAPDH.

FIG. 3. Effect of neutralizing IL-13. PBMCs were incubated with IL-13, IL-13+ anti-IL-13 mAb, or IL-13+ isotype control mAb for 24 hr and 48 hr timepoints. The level of A) CCL17 B) MDC C) CCL26 was assessed in the cell culture supernatants using ELISA.

The following experiments demonstrate that one or more of the biomarkers described herein can be used as accurate biomarker to monitor the response to anti-IL-13 therapies such as anti-IL-13 antibody therapy.

EXAMPLE 1

Microarray Experiment

Peripheral blood mononuclear cells (PBMCs) were isolated from 8 healthy donors using Ficoll and density gradient centrifugation. These were cultured in RPMI+10% FBS and left untreated or treated with IL-13 (10 ng/ml) or IL-4 (10 ng/ml) or an anti-IL-13 mAb (CNTO 607) (10 μg/ml) or human IgG1 isotype control (10 μg/ml) for 24 hrs. CNTO607 is described in U.S. provisional patent application 60/679, 925, filed May 11, 2005, and published as WO/2006/124451, which are entirely incorporated herein by reference. The IL-13 and IL-4 was purchased from R&D Systems (Minneapolis, Minn.). Total cellular RNA was isolated from the cells using the RNeasy mini kit (Qiagen, Inc. Valencia, Calif.) as per manufacturer's instructions. Samples that demonstrated high quality (ratio of 28S rRNA and 18S rRNA is greater than 1.7) were submitted for microarray analysis on the Affymetrix chip.

Microarray Processing

RNA amplification, probe synthesis and labeling, cDNA chip hybridization and washing were performed using methods well known in the art. An Agilent Image Scanner was used to scan the cDNA chips (Agilent Technologies, Palo Alto, Calif.). Fluorescence intensity for each feature of the array was obtained by using ImaGene software (BioDiscovery, Los Angeles, Calif.).

Microarray Data Analysis

In this study, Affymetrix GeneChip Human Genome U133 Plus 2.0 arrays were used to profile gene expression in human peripheral blood mononuclear cells from 10 donors stimulated with IL-13, or IL-4 at 1 time point (24 hr). Untreated samples from the same group of donors were used as control. Each array is comprised of more than 54K probe sets that analyze the expression level of over 47K transcripts and variants, including 38.5K well-characterized human genes. Raw intensity data was downloaded from DNA Chip III database. Values below 0.01 were set to 0.01. Using GeneSpring (Redwood City, Calif.; version 7.2), chip-to-chip normalization was performed by dividing the averaged intensity of each probe set by the median intensity of a chip. The intensity of each probe set was then normalized to the median intensity of that probe set in the control group. The control groups in this study were the 8 untreated samples.

A probe set was regarded as reliably detected if it was called "Present" or "Marginally Present" at least once among the 40 samples. Among 54,675 probe sets on a chip, only 36,357 probe sets passed the filtering and were analyzed further. Replicate samples were grouped according to their experimental conditions. The average of normalized intensities was used to represent each condition.

Using log 2 transformed normalized intensities, standard ANOVA was conducted in Partek Pro 6.1 (St. Charles, Mo.) to test treatment (untreated, IL13, IL4, CNTO 607, and isotype), and donor was also considered in the model as a random effect. Post-hoc tests were set up to identify genes showing significant differential expression between each treatment condition and untreated. False discovery rate cutoff was set at 0.05, meaning that 5% of identified genes would be false positives. Genes identified by statistical analysis were then filtered by fold change comparison between each treatment and untreated. The fold change cutoff was set at 1.5.

TABLE 1

The Raw And Normalized Intensities Of Each Of The Genes From Microarray Analysis And Their Gen Bank Accession Numbers

| Gene (Probe set ID) | Treatment | Average Raw Intensity | Average Normalized Intensity | GenBank Accession No. |
|---|---|---|---|---|
| CCL17 (207900_at) | Untreated | 138.8 | 1.086 | NM_002987 |
| | IL-13 | 2,268 | 17.62 | |
| | IL-4 | 2,870 | 22.42 | |
| | CNTO 607 | 130.8 | 1.005 | |
| | Isotype control | 177.1 | 1.41 | |
| CCL26 (223710_at) | Untreated | 41 | 1.64 | AF096296 |
| | IL-13 | 1883 | 72.26 | |
| | IL-4 | 1888 | 75.18 | |
| | CNTO 607 | 41.02 | 1.51 | |
| | Isotype control | 42.11 | 1.69 | |
| CCL23 (210549_s_at) | Untreated | 35.96 | 1.76 | U58913 |
| | IL-13 | 538.8 | 25.8 | |
| | IL-4 | 674.8 | 33.8 | |
| | CNTO 607 | 41.05 | 1.9 | |
| | Isotype control | 120.1 | 6.2 | |
| CCL23 (210548_at) | Untreated | 17.8 | 1.4 | U58913 |
| | IL-13 | 268.1 | 21.2 | |
| | IL-4 | 395.7 | 32.6 | |
| | CNTO 607 | 25 | 2.0 | |
| | Isotype control | 65.1 | 5.4 | |
| CCL22 (207861_at) | Untreated | 1550 | 1.2 | NM_002990 |
| | IL-13 | 4507 | 3.4 | |
| | IL-4 | 4326 | 3.3 | |
| | CNTO 607 | 1432 | 1 | |
| | Isotype control | 2636 | 2 | |
| CD1A (210325_at) | Untreated | 102.6 | 1 | M28825 |
| | IL-13 | 433.3 | 4.3 | |
| | IL-4 | 586.6 | 6 | |
| | CNTO 607 | 116.4 | 1.1 | |
| | Isotype control | 93.4 | 0.9 | |
| CD1B (206749_at) | Untreated | 104.7 | 1 | NM_001764 |
| | IL-13 | 1715 | 17.6 | |
| | IL-4 | 2142 | 22.5 | |
| | CNTO 607 | 92.9 | 0.9 | |
| | Isotype control | 84.62 | 0.9 | |
| CD1C (205987_at) | Untreated | 347.1 | 1 | NM_001765 |
| | IL-13 | 4251 | 12.79 | |
| | IL-4 | 4864 | 15.01 | |
| | CNTO 607 | 353 | 1 | |
| | Isotype control | 289.8 | 0.9 | |
| WNT5A (205990_s_at) | Untreated | 33.7 | 0.8 | NM_003392 |
| | IL-13 | 958.1 | 23.6 | |
| | IL-4 | 1091 | 27.1 | |
| | CNTO 607 | 40 | 0.9 | |
| | Isotype control | 111.5 | 2.7 | |

TABLE 1-continued

The Raw And Normalized Intensities Of Each Of The Genes From Microarray Analysis And Their Gen Bank Accession Numbers

| Gene (Probe set ID) | Treatment | Average Raw Intensity | Average Normalized Intensity | GenBank Accession No. |
|---|---|---|---|---|
| WNT5A (213425_at) | Untreated | 32.1 | 1.4 | NM_003392 |
| | IL-13 | 390.6 | 17.6 | |
| | IL-4 | 463.2 | 21 | |
| | CNTO 607 | 31.6 | 1.4 | |
| | Isotype control | 64.2 | 2.8 | |
| WNT5A (231227_at) | Untreated | 35.8 | 1.7 | NM_003392 |
| | IL-13 | 248.8 | 11.7 | |
| | IL-4 | 256.4 | 12.2 | |
| | CNTO 607 | 20.9 | 1 | |
| | Isotype control | 38 | 1.8 | |
| IgE CD23A (206759_at) | Untreated | 106.8 | 1 | NM_002002 |
| | IL-13 | 2811 | 28.4 | |
| | IL-4 | 3399 | 35.3 | |
| | CNTO 607 | 99.5 | 1 | |
| | Isotype control | 210.4 | 2.2 | |
| IgE CD23A (206760_s_at) | Untreated | 58.4 | 1.4 | NM_002002 |
| | IL-13 | 2091 | 49.4 | |
| | IL-4 | 2321 | 56.2 | |
| | CNTO 607 | 27.2 | 0.6 | |
| | Isotype control | 52.7 | 1.2 | |
| hIL-17 R beta (219255_x_at) | Untreated | 83.2 | 2.3 | NM_018725 |
| | IL-13 | 379.7 | 10.3 | |
| | IL-4 | 372.5 | 10.3 | |
| | CNTO 607 | 122.7 | 3.3 | |
| | Isotype control | 149.3 | 4.2 | |
| hIL-17 R beta (224156_x_at) | Untreated | 123.9 | 1.1 | NM_018725 |
| | IL-13 | 447 | 4 | |
| | IL-4 | 405.6 | 3.7 | |
| | CNTO 607 | 153.2 | 1.3 | |
| | Isotype control | 180.2 | 1.6 | |
| hIL-17 R beta (224361_s_at) | Untreated | 100.9 | 1.2 | NM_018725 |
| | IL-13 | 362.9 | 4.5 | |
| | IL-4 | 340.2 | 4.3 | |
| | CNTO 607 | 128.3 | 1.6 | |
| | Isotype control | 145.5 | 1.8 | |

After analyzing the microarray data it became apparent that both IL-13 and IL-4 generated a very similar expression profile i.e., genes upregulated by IL-13 were the same as those upregulated by IL-4 at the 1.5 fold cutoff. All of these genes were up regulated with IL-4 and IL-13 when compared to untreated but CNTO 607 or isotype control, as shown in Table 1. From this data, a list of potential biomarkers was generated (Table 2). FIG. 2 shows a graphical representation of the microarray data for four of the biomarkers.

TABLE 2

Potential Biomarkers Associated With IL-13 Biology

CCL17 (TARC thymus & activation regulated chemokine)
CCL26 (Eotaxin 3)
CCL23 (MPIF-1 myeloid progenitor inhibitory factor 1)
CCL22 (MDC macrophage derived chemokine)

TABLE 2-continued

Potential Biomarkers Associated With IL-13 Biology

CD1 A, B, C
WNT5A
IgE CD23A
hIL-17 R beta

For some of the genes more than one probe set was detected by microarray further confirming the results.

Real Time PCR (TaqMan) Confirmation:

In order to confirm the microarray findings by an independent means, Real Time PCR technology was employed. Total RNA from PBMCs cultured in the presence of IL-13 (10 ng/ml) or IL-4 (10 ng/ml) or CNTO 607 (10 µg/ml) or human IgG1 isotype control (10 µg/ml) for 24 hrs was reverse transcribed and used in Real Time PCR analysis for each of the 10 genes using the Applied Biosystems Gene Expression Assays on Demand on the ABI PRISM® 7900HT Sequence Detection System.

The Real Time PCR was conducted as follows. 1 µg of total RNA from each of the treated and untreated groups of PBMCs were used for the reverse transcription (RT) reaction. The RT reaction was performed as per protocol using TaqMan® RT reagents (Applied Biosystems) at 37° C. for 120 min followed by 25° C. for 10 min. Forty ng of cDNA per reaction were used in the Real Time PCR using the ABI Prism® 7900 sequence detection system (Foster City, Calif.). In the presence of AmpliTaq Gold DNA polymerase (ABI Biosystems, Foster City, Calif.), the reaction was incubated for 2 min at 50° C. followed by 10 min at 95° C. Then the reaction was run for 40 cycles at 15 sec, 95° C. and 1 min, 60° C. per cycle. Assays-on-Demand™ primers and probes (Applied Biosystems) were used in the PCR. The Real Time PCR data was analyzed using the standard curve method.

TABLE 3

The Mean RNA Quantity For Each Of The Genes At Various Treatment Conditions Using Taqman

| Gene | Treatment | Mean RNA quantity (Normalized to GAPDH) | Assay ID # |
|---|---|---|---|
| CCL17 | Untreated | 0.96 | Hs00171074_m1 |
| | IL-13 | 289.6 | |
| | IL-4 | 489 | |
| | CNTO 607 | 0.96 | |
| | Isotype control | 2.4 | |
| CCL26 | Untreated | Undetected | Hs00171146_m1 |
| | IL-13 | 1.1 | |
| | IL-4 | 1.3 | |
| | CNTO 607 | Undetected | |
| | Isotype control | Undetected | |
| CCL23 | Untreated | 0.57 | Hs00270756_m1 |
| | IL-13 | 5.6 | |
| | IL-4 | 6.3 | |
| | CNTO 607 | 0.5 | |
| | Isotype control | 1.24 | |
| CCL22 | Untreated | 1.4 | Hs00171080_m1 |
| | IL-13 | 5.1 | |
| | IL-4 | 5.1 | |
| | CNTO 607 | 1.3 | |
| | Isotype control | 2.4 | |

TABLE 3-continued

The Mean RNA Quantity For Each Of The Genes At Various Treatment Conditions Using Taqman

| Gene | Treatment | Mean RNA quantity (Normalized to GAPDH) | Assay ID # |
|---|---|---|---|
| CD1A | Untreated | 1.1 | Hs00233332_m1 |
| | IL-13 | 32.4 | |
| | IL-4 | 42.5 | |
| | CNTO 607 | 0.79 | |
| | Isotype control | 1 | |
| CD1B | Untreated | 1.3 | Hs00233507_m1 |
| | IL-13 | 30.5 | |
| | IL-4 | 38.4 | |
| | CNTO 607 | 1.1 | |
| | Isotype control | 1.4 | |
| CD1C | Untreated | 0.9 | Hs00233509_m1 |
| | IL-13 | 18.3 | |
| | IL-4 | 19.8 | |
| | CNTO 607 | 0.77 | |
| | Isotype control | 0.5 | |
| WNT5A | Untreated | 1.2 | Hs00180103_m1 |
| | IL-13 | 147 | |
| | IL-4 | 190.4 | |
| | CNTO 607 | 2.1 | |
| | Isotype control | 7.2 | |
| IgE CD23A | Untreated | 0.79 | Hs00233627_m1 |
| | IL-13 | 33.3 | |
| | IL-4 | 35.8 | |
| | CNTO 607 | 0.7 | |
| | Isotype control | 1.4 | |
| hIL-17 R beta | Untreated | 0.7 | Hs00218889_m1 |
| | IL-13 | 6 | |
| | IL-4 | 5.8 | |
| | CNTO 607 | 0.7 | |
| | Isotype control | 1.1 | |

As shown in Table 3, CCL17, CCL22, CCL23 and CCL26 were all upregulated by IL-13 or IL-4 while their expression was not modulated by anti-IL-13 mAb or the isotype control mAb. This is comparable to the microarray data set forth in Table 1.

EXAMPLE 2

In order to validate the modulation of genes by IL-13 at the protein level, ELISA was used to detect protein in cell culture supernatants and confirm upregulation of CCL17, CCL22 and CCL26 by IL-13. As shown in FIG. 3, IL-13 (10 ng/ml, 24 hr and 48 hr) stimulates the protein expression of CCL17, CCL22 and CCL26. Also neutralization of IL-13 by an anti-IL-13 mAb results in a down regulation of IL-13 induced CCL17, CCL22 and CCL26.

PBMC Culture and ELISA

PBMCs were cultured with IL-13 (10 ng/ml), IL-13 (10 ng/ml) plus anti-IL-13 therapeutic antibody, CNTO 607 (2 μg/ml) or IL-13 (10 ng/ml) plus isotype control mAb, human IgG1 (2 μg/ml) for 24 and 48 hr time points.

The PBMC culture supernatant was assayed for TARC protein using a human TARC ELISA assay (R&D Systems) and for MDC protein using a human MDC ELISA assay (R&D Systems). The data showed that the neutralization of IL-13 by CNTO 607 resulted in a down regulation of IL-13 induced TARC and MDC at the protein level (Table 4). These data suggest that TARC and MDC could serve as potential biomarkers in an anti-IL-13 clinical study.

TABLE 4

Mean Protein Level In PBMC Culture Supernatants From N = 5 Donors Following Various Treatment Conditions

| Treatment | Time point | TARC (pg/ml) | MDC (pg/ml) |
|---|---|---|---|
| Untreated | 24 hr | 0.6 | 70.6 |
| IL-13 (10 ng/ml) | 24 hr | 89 | 519.4 |
| IL-13 (10 ng/ml) + human IgG1 (2 μg/ml) | 24 hr | 86.2 | 473.6 |
| IL-13 (10 ng/ml) + CNTO 607 (2 μg/ml) | 24 hr | 0.8 | 93.2 |
| Untreated | 48 hr | 2 | 110 |
| IL-13 (10 ng/ml) | 48 hr | 287 | 851.2 |
| IL-13 (10 ng/ml) + human IgG1 (2 μg/ml) | 48 hr | 361.6 | 1398.2 |
| IL-13 (10 ng/ml) + CNTO 607 (2 μg/ml) | 48 hr | 2.4 | 240.2 |

The role of biomarkers is becoming increasingly important in the clinical development of therapeutics. Their role ranges from, stratifying the patient population in helping to identify responders versus non-responders, to determining the efficacy of the therapeutic. Biomarkers can be a valuable tool in making better decisions that will reduce the cost for drug development and enable therapies to reach the right patient population faster.

What is claimed is:

1. A method for monitoring a response to IL-13 therapy in a patient undergoing IL13 therapy by measuring IL-13 associated-biomarker total RNA expression, comprising:
   (a) in a first PBMC sample taken from a patient to be administered with IL-13 therapy, measuring the total RNA expression of a biomarker selected from the group consisting of WNT5A and MPIF-1(CCL23);
   (b) administering IL-13 therapy to said patient;
   (c) in a second PBMC sample taken from said patient after administering said IL-13 therapy, measuring the total RNA expression of a biomarker selected from the group consisting of WNT5A and MPIF-1 (CCL23); and
   (d) comparing between the first and second PBMC samples, the level of biomarker total RNA expression, wherein said biomarker is selected from the group consisting of WNT5A and MPIF-1 (CCL23)
   wherein a reduction in biomarker expression is indicative of a reduction in IL-13 activity following administering said IL-13 therapy.

2. The method of claim 1 wherein said IL-13 therapy is for the treatment of asthma, COPD or emphysema.

3. The method of claim 1 wherein the anti-IL-13 therapy is the administration of an anti-IL-13 antibody.

4. The method of claim 1, wherein said measuring of steps (a) and (c) further include the step of measuring the total RNA expression of a biomarker selected from the group consisting of: CCL17 (TARC), CCL22 (MDC), CCL23 (MPIF-1) and CCL26 (Eotaxin 3), CD1A, CD1B, CD1C, IgE CD23A, and IL-17Rbeta (GenBank Accession No. NM_018725).

5. The method of claim 1 wherein said biomarker is CCL23 (MPIF-1).

6. The method of claim 1 wherein said biomarker is WNT5A.

* * * * *